United States Patent
Brandt et al.

(10) Patent No.: US 6,828,438 B2
(45) Date of Patent: Dec. 7, 2004

(54) PROCESS FOR THE PREPARATION OF THE SODIUM SALT OF 6[D-(-)α-4-(ETHYL-2,3-DIOXO-1-PIPERAZINOCARBONYLAMINO) PHENYLACETAMIDO]PENICILLANIC ACID

(75) Inventors: Alberto Brandt, Rome (IT); Loredana Cecchetelli, Genzano (IT); Giordano Bruno Corsi, Genzano (IT); Antonio Simeoni, Pomezia (IT)

(73) Assignee: Istituto Biochimico Italiano Giovanni Lorenzini S.p.A., Milan (IT)

( * ) Notice: Subject to any disclaimer, the term of this patent is extended or adjusted under 35 U.S.C. 154(b) by 0 days.

(21) Appl. No.: 10/210,563

(22) Filed: Aug. 1, 2002

(65) Prior Publication Data

US 2003/0028016 A1 Feb. 6, 2003

(30) Foreign Application Priority Data

Aug. 3, 2001 (IT) ..................................... MI2001A1718

(51) Int. Cl.$^7$ ..................... C07D 499/16; C07D 499/76
(52) U.S. Cl. ..................................... 540/323; 540/333
(58) Field of Search ................... 540/323, 333

(56) References Cited

U.S. PATENT DOCUMENTS

| 4,112,090 A | | 9/1978 | Saikawa et al. ............. 424/251 |
| 4,837,317 A | * | 6/1989 | Ratti .......................... 540/316 |
| 6,207,661 B1 | * | 3/2001 | Thompson et al. ......... 514/192 |

FOREIGN PATENT DOCUMENTS

| EP | 0 294 789 A1 | 12/1988 | ......... C07D/499/68 |
| EP | 0 596 262 A1 | 5/1994 | ......... C07D/499/16 |
| GB | 2 179 348 A | 3/1987 | ......... C07D/499/68 |

* cited by examiner

Primary Examiner—Mark L. Berch
(74) Attorney, Agent, or Firm—Morgan & Finnegan, L.L.P.

(57) ABSTRACT

The present invention refers to the preparation process of the sodium salt of 6[D-(-)α-4-(ethyl-2,3-dioxo-1-piperazinocarbonylamino) phenylacetamido]penicillanic acid, comprising the reaction of the acid with a reagent selected from the group consisting of sodium hydroxide, sodium carboxylates and sodium alcoholates, followed by a separation step of the so obtained sodium salt by precipitation.

24 Claims, No Drawings

US 6,828,438 B2

PROCESS FOR THE PREPARATION OF THE SODIUM SALT OF 6[D-(-)α-4-(ETHYL-2,3-DIOXO-1-PIPERAZINOCARBONYLAMINO) PHENYLACETAMIDO]PENICILLANIC ACID

FIELD OF THE INVENTION

The present invention refers to a preparation process of the sodium salt of 6[D-(-)α-4-(ethyl-2,3-dioxo-1-piperazinocarbonylamino)phenylacetamido]penicillanic acid, useful as active ingredient in the treatment of pneumonia, peritonitis and blood infection.

STATE OF THE ART

Many preparation processes of the sodium salt of penicillanic acids and, in particular of 6[D-(-)α-4-(ethyl-2,3-dioxo-1-piperazinocarbonylamino) phenylacetamido] penicillanic acid are already known.

By way of example, mention is made of the processes described in the European Patent Application No. EP 294 789 or in the U.S. Pat. No. 4,112,090. Such processes, when scaled up to industrial level, show considerable drawbacks, especially when they are meant for the production of a sterile sodium salt. For example, when the salification is carried out with sodium 2-ethyl hexanoate, the sodium salt content, determined in the salification product by HPLC, is low because of the large amount of hexanoic acid that forms and remains in the final product as an hardly eliminable residue. Conversely, when the penicillanic acid is salified with a strong base, such as sodium hydroxide or sodium methoxide or sodium ethoxide, the molecule of the acid—due to the highly alkaline medium—can degrade giving hardly eliminable by-products, if the salt is separated by crystallisation.

These are the reasons why the commercially available sodium salt of 6[D-(-)α-4-(ethyl-2,3-dioxo-1-piperazinocarbonylamino)phenylacetamido]penicillanic acid is now produced by lyophilisation, which procedure does not require acid purification. Therefore, the need for a scalable process of preparation of the sodium salt of 6[D-(-)α-4-(ethyl-2,3-dioxo-1-piperazinocarbonylamino) phenylacetamido] penicillanic acid, in particular in the sterile form is deeply felt.

SUMMARY

The Applicant has found that the sodium-salt of 6[D-(-)α-4-(ethyl-2,3-dioxo-1-piperazinocarbonylamino) phenylacetamido]penicillanic acid can be prepared, also industrially, and separated by precipitation from the solution in which it forms, under operating conditions envisaging the use, in the salification, of the acid and bases in the form of solutions, thus obtaining a high-purity final product in high yields.

It is therefore subject of the invention to provide a preparation process of the sodium salt of 6[D-(-)α-4-(ethyl-2,3-dioxo-1-piperazinocarbonylamino)phenylacetamido] penicillanic acid, comprising the reaction of a solution of the 6[D-(-)α-4-(ethyl-2,3-dioxo-1-piperazinocarbonylamino) phenylacetamido] penicillanic acid with a solution of a reagent selected from the group consisting of sodium hydroxide, sodium carboxylates and sodium alcoholates in suitable organic solvents or organic solvents mixtures, followed by the separation by precipitation of the resulting sodium salt.

By maintaining the reagents in solution as indicated above, the process of the invention can be carried out according to various operating procedures.

According to a first embodiment of the invention, the solutions of the above mentioned penicillanic acid and of the above mentioned basic reagent chosen from sodium hydroxide, sodium carboxylates- and sodium alcoholates can be prepared in a non-sterile environment, then both solutions are subjected to sterilising filtration, and the sodium salt is precipitated in a sterile environment.

According to a second embodiment of the present process the solution of the basic reagent and the solution of the salified acid are prepared in a non-sterile environment; both solutions are then subjected to sterilising filtration, and the sodium salt is precipitated in a sterile environment, possibly by addition of a suitably sterilised non-solvent.

According to a third embodiment of the present process a sodium salt solution of the acid is prepared in a non-sterile environment; the solution is then sterilised, and the sodium salt is precipitated in a sterile environment by addition of a non-solvent previously subjected to sterilising filtration.

By operating according to the first embodiment of the invention mentioned above, the acid solution is obtained in a concentration ranging from 2% to 10% by wt. in respect of the total volume of the acid solution, and the basic solution in a concentration comprised between 2% and 10% by wt. in respect of the total volume of the basic solution.

In the second embodiment of the invention mentioned above, a basic solution having a concentration comprised between 2% and 10% by wt. in respect of the total volume of the basic solution is used, and a solution of the acid pre-salified with an organic base (the concentration of salt in this solution is up to 50%, and preferably comprised between 30 and 50% by wt. in respect of the total volume of this solution).

In the third embodiment of the invention mentioned above, a sodium salt solution of the acid is used in a concentration up to 20%, and preferably comprised between 10 and 20% by wt. in respect of the total volume of this solution.

It is a further subject of the invention the crystalline sodium salt of 6[D-(-)α4-(ethyl-2,3-dioxo-1-piperazinocarbonylamino)phenylacetamido] penicillanic acid in the monohydrated form.

The characteristics and advantages of the process according to the present invention will be apparent from the detailed description that follows.

DETAILED DESCRIPTION OF THE INVENTION

The 6[D-(-)α-4-(ethyl-2,3-dioxo-1-piperazinocarbonylamino)phenylacetamido] penicillanic acid, prepared according to methods known in the art, e.g. as described in Italian patent application No. MI2001A001021 in the name of the Applicant, is converted into the corresponding sodium salt by reaction with a reagent selected from the group consisting of sodium hydroxide, sodium carboxylates, preferably sodium 2-ethyl hexanoate, and sodium alcoholates, preferably sodium methoxide and sodium ethoxide.

The salification reaction according to the invention is carried out by dissolving the above said penicillanic acid and the above said reagent chosen from sodium hydroxide, sodium carboxylates and sodium alcoholates, in a suitable organic solvent or in a mixture of solvents, so as to obtain a limpid solution, in which the acid and the reagent are completely dissolved and from which the sodium salt precipitates.

According to an embodiment of the present process, the above said penicillanic acid and the above said reagent are dissolved separately in suitable organic solvents, or in solvent mixtures, so to obtain two limpid solutions that, once sterilised by filtration and mixed in a sterile environment, give rise to the precipitation of the desired sterile sodium salt.

The above said organic solvents or solvent mixtures must be suitable for dissolving the acid and the reagent, but must be also miscible with each other, thus securing the formation of a homogeneous mixture wherefrom the sterile sodium salt precipitates, possibly by addition of a non-solvent.

Solvents that, according to the invention, are suitable for the dissolution of the above said penicillanic acid are selected from the group consisting of acetone, acetonitrile, alcohols, preferably isopropyl alcohol, and mixtures thereof; acetone is the preferred solvent for the dissolution of 6[D-(-)α-4-(ethyl-2,3-dioxo-1-piperazinocarbonylamino) phenylacetamido] penicillanic acid.

When the reagent is sodium 2-ethyl hexanoate, the solvents suitable for dissolving the reagent are selected from the group consisting of ethyl acetate, acetone, acetonitrile, isopropyl alcohol and mixtures thereof; ethyl acetate is preferred. When the reagent is sodium hydroxide or sodium methoxide or sodium ethoxide, the reagent may be dissolved by alcohols, preferably ethanol or methanol; ethanol is particularly preferred.

Water may be added to the acid solution and/or to the basic solution in order to favour the crystallisation of the final sodium salt.

The non-solvent according to the invention may be selected for example from the group consisting of acetone, methyl isobutyl ketone, acetonitrile, ethyl acetate and mixtures thereof.

The term "non-solvent" is used herein to indicate a solvent in which the product in question is not soluble or in negligible amount soluble.

As already mentioned above, the initial concentration of the above said penicillanic acid preferably ranges from 2% to 10% by wt. in respect of the solution total weight, and more preferably from 5% to 6%.

Alternatively, the present process can be implemented also starting from more concentrated solutions of the penicillanic acid, provided that the penicillanic acid is previously salified with a suitable organic base, chosen for example from between diethylamine and triethylamine, and subsequently the organic base is displaced with the strong base represented by the aforesaid reagent.

According to the present process, the amount of the above mentioned reagent may range from 1.0 to 1.1 mol per mol of acid and preferably is 1.02 mol per mol of acid.

When sodium hydroxide and sodium alcoholates are used for preparing the basic solution, the salification reaction of the basic solution with penicillanic acid is preferably carried out at a temperature ranging from −10° C. to −30° C.

When sodium carboxylates are used in the basic solution, the salification reaction of the acid is carried out at a temperature preferably ranging from 15° C. to 25° C.

The sodium salt that forms as described above according to the present process, is then separated by precipitation, followed by filtration.

When the precipitation is carried out in an organic solvent in the presence of water, the sodium salt of 6[D-(-)α-4-(ethyl-2,3-dioxo-1-piperazinocarbonylamino) phenylacetamido]penicillanic acid is obtained in the monohydrated form.

After drying the so obtained sodium salt at a temperature lower than 60° C. for 4 to 6 hours under vacuum (10 mbar), the product has a water content greater than 3%.

The sodium salt of 6[D-(-)α-4-(ethyl-2,3-dioxo-1-piperazinocarbonylamino)phenylacetamido] penicillanic acid in monohydrate form represents a further subject of the present invention.

The following examples are given to provide non-limiting illustrations of the present invention.

EXAMPLE 1

Preparation of the Sodium Salt of 6[D-(-)α-4-(ethyl-2,3-dioxo-1-piperazinocarbonylamino)phenylacetamido] penicillanic Acid The three following solutions were prepared:
SOLUTION A) 60 g of 6[D-(-)α-4-(ethyl-2,3-dioxo-1-piperazinocarbonylamino) phenylacetamido]penicillanic acid was dissolved in 900 ml of acetone and 9 ml of methanol, at a temperature of approx. 20° C. Once the solubilisation was completed, the solution was added with 1.2 ml of water.
SOLUTION B) 19.8 g of sodium 2-ethyl hexanoate was dissolved in 210 ml of acetone at 20° C. Once the solubilisation was completed, the solution was added with 1.2 ml of water.
SOLUTION C) 420 ml of acetone and 1.2 ml of water were mixed.

SOLUTION B) was thread-poured into SOLUTION A) with vigorous stirring; as soon as the formation of the precipitate was observed, the addition of SOLUTION C) was started so as to conclude A) and C) additions at the same time. This reaction mixture was cooled to 0° C. to 3° C. and maintained at said temperature for 2 hrs; then the product was filtered on Buchner.

The resulting product was suspended again with 500 ml of acetone, allowed to stir for 30 min, filtered and further washed with 500 ml of acetone. The product was oven dried under vacuum at approx. 50° C. for 8 hrs.

54 g of 6[D-(-)α-4-(ethyl-2,3-dioxo-1-piperazinocarbonylamino)phenylacetamido]penicillanic acid in the form of sodium salt monohydrate was obtained (sodium salt content by HPLC 98.36% (anhydrous basis), water quantity, calculated by Karl Fisher's method, 3.2%).

EXAMPLE 2

Preparation of the Sodium Salt of 6[D-(-)α-4-(ethyl-2,3-dioxo-1-piperazinocarbonylamino)phenyl acetamido] penicillanic Acid The three following solutions were prepared:
SOLUTION A) prepared as per Example 1
SOLUTION B) prepared as per Example 1
SOLUTION C) 420 ml of acetone, 18 ml of methyl isobutyl ketone and 2.8 ml of water were mixed.

The method of Example 1 was followed to give 55.1 g of 6[D-(-)α-4-(ethyl-2,3-dioxo-1-piperazinocarbonylamino) phenylacetamido] penicillanic acid in the form of sodium salt monohydrate (sodium salt content by HPLC 96.74% (anhydrous basis), water quantity, calculated by Karl Fisher's method, 3.3%).

EXAMPLE 3

Preparation of the Sodium Salt of 6[D-(-)α-4-(ethyl-2,3-dioxo-1-piperazinocarbonylamino)phenyl acetamido] penicillanic Acid The two following solutions were prepared:
SOLUTION A) 120 g of 6[D-(-)α-4-(ethyl-2,3-dioxo-1-piperazinocarbonylamino) phenylacetamido]penicillanic acid was dissolved in 250 ml of acetone; 31.6 ml of triethylamine was added during 5 min with vigorous stirring, which was continued until complete dissolution.
SOLUTION B) 39.6 g of sodium 2-ethyl hexanoate was dissolved in 1,000 ml of acetone at 15° C.

SOLUTION A) was thread-poured into SOLUTION B) with vigorous stirring at a temperature of 15□ to 18° C. Once the addition was completed, the rate of stirring was reduced to 20–30 rpm, while the temperature was maintained at 15° to 18° C. for 90 min.

The resulting product was recovered by filtration, washed and suspended again twice with 500 ml of acetone. The product was oven dried under vacuum at approx. 35° C. for 8 hrs. 104 g of a white amorphous product, which was found to be 6[D-(−)α-4-(ethyl-2,3-dioxo-1-piperazinocarbonylamino) phenylacetamido]penicillanic acid in the form of sodium salt, was obtained (yield 87% by wt.; sodium salt content by HPLC 95.80%).

EXAMPLE 4
Preparation of the Sodium Salt of 6[D-(−)α-4-(ethyl-2.3-dioxo-1-piperazinocarbonylamino)phenyl acetamido] penicillanic Acid A 1 l flask was fed with 182.5 ml of isopropyl alcohol, 182.5 ml of acetonitrile and 182.5 ml of acetone. 100 g of 6[D-(−)α-4-(ethyl-2,3-dioxo-1-piperazinocarbonylamino) phenyl acetamido]penicillanic acid was added portionwise under vigorous stirring. Stirring was continued for approx. 15 min until complete solubilisation. The solution was then added with 8.3 ml of water and allowed to stir for additional 5 min.

33.2 g of sodium 2-ethyl hexanoate was added portion-wise over 15 to 20 min. The solution was allowed to stir for approx. 30 min until complete solubilisation. The resulting solution was fed, over approx. 15 min and with vigorous stirring, to a 3 l flask containing 1,825 ml acetone.

The 1 l flask that had contained the solution was washed with a mixture consisting of 3.6 ml of acetone, 3.6 ml of acetonitrile and 3.6 ml of isopropyl alcohol. This mixture was then fed to the 3 l flask and stirred at a temperature of 20° C. for 30 min.

The precipitate was recovered by filtration, piston washed with 170 ml of acetone, suspended again with 340 ml of acetone, stirred for 30 min, and further piston washed with 170 ml of acetone.

The resulting product was dried under vacuum at 50° C. for 6 hrs. 86 g of [D-(−)α-4-(ethyl-2,3-dioxo-1-piperazinocarbonylamino)phenylacetamido] penicillanic acid in the form of sodium salt monohydrate was obtained (yield 86% by wt.; sodium salt content by HPLC 97.50%).

EXAMPLE 5
Preparation of the Sodium Salt of 6[D-(−)α-4-(ethyl-2,3-dioxo-1-piperazinocarbonylamino)phenyl acetamido] penicillanic Acid A 1 l flask was fed with 182.5 ml of isopropyl alcohol, 182.5 ml of acetonitrile and 182.5 ml of acetone. 100 g of 6[D-(−)α-4-(ethyl-2,3-dioxo-1-piperazino carbonylamino) phenyl acetamido] penicillanic acid was added portionwise with vigorous stirring. Stirring was continued for approx. 15 min until complete solubilisation.

33.2 g of sodium 2-ethyl hexanoate was added portion-wise over 15 to 20 min. The solution was allowed to stir for approx. 30 min until complete solubilisation. The resulting solution was fed, over approx. 30 min and with vigorous stirring, to a 3 l flask containing 1,825 ml of acetone.

The 1 l flask that had contained the solution was washed with a mixture consisting of 3.6 ml of acetone, 3.6 ml of acetonitrile and 3.6 ml of isopropyl alcohol. This mixture was then fed to the 3 l flask and stirred at a temperature of 20° C. for 90 min.

The precipitate was recovered by filtration, piston washed with 510 ml of acetone, suspended again with 510 ml of acetone, stirred for 30 min, and further piston washed with 510 ml of acetone.

The resulting product was dried under vacuum at 65° C. for 6 hours.

90 g of [D-(−)α-4-(ethyl-2,3-dioxo-1-piperazinocarbonylamino)phenylacetamido]penicillanic acid in the form of sodium salt was obtained (yield 90% by wt.; anhydrous sodium salt content by HPLC 97%).

EXAMPLE 6
Preparation of the Sodium Salt of 6[D-(−)α-4-(ethyl-2,3-dioxo-1-piperazinocarbonylamino)Phenyl Acetamido] Penicillanic Acid A 100 ml glass flask was fed with 70 ml of abs. ethanol and 1.92 g of sodium hydroxide. The mixture was allowed to stir for 35 to 40 min until complete solubilisation. The solution was filtered and maintained in a sealed flask. The flask in which the solubilisation took place and the filter were washed with 10 ml of ethanol.

A 1,000 ml glass flask, provided with stirrer, was fed with 900 ml of acetone and, with stirring at 220 rpm, with 25 g of 6[D-(−)α-4-(ethyl-2,3-dioxo-1-piperazinocarbonylamino)phenyl acetamido]penicillanic acid. The mixture was allowed to stir for approx. 10 min until complete solubilisation. The solution, still under stirring at 220 rpm, was cooled to −25° to −30° C., and added, from a dropping funnel, during 30 to 35 min, with a sodium hydroxide solution prepared as mentioned above. Once the additions were completed, stirring at 220 rpm was continued for 10 min; then the stirring rate was reduced to 120 rpm. The cooling bath was removed and the temperature was allowed to rise to 0° to 5° C. The resulting product was filtered, washed with 200 ml of acetone (100 ml×2), and dried at 70° C. for 6 hours.

23 g of the sodium salt of [D-(−)α-4-(ethyl-2,3-dioxo-1-piperazinocarbonylamino)phenylacetamido]penicillanic acid was obtained (yield 92% by wt.; sodium salt content by HPLC (anhydrous basis) 97%).

EXAMPLE 7
Preparation of the Sodium Salt of 6[D-(−)α-4-(ethyl-2.3-dioxo-1-piperazinocarbonylamino)Phenyl Acetamido] Penicillanic Acid A 100 ml glass flask was fed with 70 ml of abs. ethanol and 2.6 g of sodium methoxide. The mixture was allowed to stir for 30 to 35 min until complete solubilisation. The solution was filtered and maintained in a sealed flask. The flask in which the solubilisation took place and the filter were washed with 10 ml of ethanol.

A 1,000 ml glass flask, provided with stirrer, was fed with 900 ml of acetone and, with stirring at 220 rpm, with 25 g of 6[D-(−)α-4-(ethyl-2,3-dioxo-1-piperazinocarbonylamino)phenylacetamido]penicillanic acid. The mixture was allowed to stir for approx. 10 min until complete dissolution. The solution, still with stirring at 220 rpm, was cooled to −20° to −25° C. and then added, from a dropping funnel, during 30 to 35 min with a sodium methoxide solution prepared as mentioned above. Once the additions were completed, stirring at 220 rpm was continued for 10 min; then the stirring rate was reduced to 120 rpm. The cooling bath was removed and the temperature was allowed to rise to 8° to 10° C. The resulting product was filtered, washed with 200 ml of acetone (100 ml×2) and dried at 70° C. for 6 hours.

22 g of the sodium salt of [D-(−)α-4-(ethyl-2,3-dioxo-1-piperazinocarbonylamino)phenylacetamido]penicillanic acid was obtained (yield 88% by wt.; sodium salt content by HPLC (anhydrous basis) 97.2%).

EXAMPLE 8
Preparation of the Sodium Salt of 6[D-(−)α-4-(ethyl-2,3-dioxo-1-piperazinocarbonylamino)Phenyl Acetamido] Penicillanic Acid A 100 ml glass flask was fed with 70 ml of abs. ethanol and 3.4 g of sodium ethoxide during approx. 10 min. The temperature was controlled by means of an external cooling bath. Once the additions were completed, upon complete product solubilisation, the temperature was allowed to rise to 23° to 25° C. The solution was filtered and maintained in a sealed flask. The flask in which the solubilisation took place and the filter were washed with 10 ml ethanol.

A 1,000 ml glass flask provided with stirrer was fed with 900 ml acetone and, with stirring at 220 rpm, with 25 g of 6[D-(−)α-4-(ethyl-2,3-dioxo-1-piperazinocarbonylamino) phenylacetamido]penicillanic acid. The mixture was allowed to stir for approx. 10 min until complete dissolution. The solution, still with stirring at 220 rpm, was cooled to −20° to −25° C. and added, from a dropping funnel, during 30 to 35 min with a sodium methoxide solution prepared as mentioned above. Once the additions were completed, stirring at 220 rpm was continued for 10 min; then the stirring rate was reduced to 120 rpm. The cooling bath was removed and the temperature was allowed to rise to 8° to 10° C. The resulting product was filtered, washed with 200 ml of acetone (100 ml×2), and dried at 70° C. for 6 hours.

22 g of the sodium salt of [D-(−)α-4-(ethyl-2,3-dioxo-1-piperazinocarbonylamino)phenylacetamido]penicillanic acid was obtained (yield 88% by wt.; sodium salt content by HPLC (anhydrous basis) 96.8%).

EXAMPLE 9
Preparation of the Sodium Salt of 6[D-(−)α-4-(ethyl-2,3-dioxo-1-piperazinocarbonylamino)Phenyl Acetamido] Penicillanic Acid A 500 ml glass flask was fed with 240 ml of ethyl acetate and 8.29 g of sodium 2-ethyl hexanoate. The mixture was solubilised at room temperature.

A 2,000 ml glass flask, provided with stirrer, was fed with 425 ml of acetone and, under stirring at 220 rpm, with 25 g of 6[D-(−)α-4-(ethyl-2,3-dioxo-1-piperazinocarbonylamino)pheny acetamido]penicillanic acid. The mixture was allowed to stir for approx. 10 min until complete solubilisation. The solution, still with stirring at 220 rpm at room temperature, was added, from a dropping funnel, during 30 min, with the sodium 2-ethyl hexanoate solution prepared as mentioned above. Once the additions were completed, stirring at 60 to 80 rpm was continued at a temperature of 22° to 25° C. for 90 min. The resulting product was filtered, washed with 300 ml of acetone (100 ml×3), and dried at 600 to 65° C. for 6 hrs.

23 g of the sodium salt of [D-(−)α-4-(ethyl-2,3-dioxo-1-piperazinecarbonylamino) phenylacetamido]penicillanic acid was obtained (yield 92% by wt., sodium salt content by HPLC (anhydrous basis) 98.50%, water quantity, calculated by the Karl Fischer's method, 0.9%).

EXAMPLE 10
Preparation of the Sodium Salt of 6[D(−)-α-(4-ethyl-2.3-dioxo-1-piperazinecarbonylamino)phenylacetamido] penicillanic Acid In a 1,000 ml glass flask 400 ml of acetone are introduced, then 33 g of sodium 2-ethylhexanoate are added and solubilised at a temperature of 20±2° C.

In a 4,000 ml glass flask with a stirrer 2000 ml of acetone are introduced, and put under stirring at 220 rpm and temperature of 20±2° C.; 100 g of 6[D(−)-α-(4-ethyl-2,3-dioxo-1-piperazinecarbonylamino)phenylacetamido] penicillanic acid are then added, and the mixture is maintained under stirring until the solubilisation is complete (about 10/15 minutes). Under stirring 22 ml of methyl alcohol are added, then 22 ml of water are added after 5 minutes. When the solution is limpid, 400 ml of acetone are added.

The solution is maintained under stirring at 120–130 rpm and at the temperature of 20±2° C., the solution of sodium 2-ethylhexanoate, prepared as described above, is added in 5 minutes by means of a drip funnel. Once the addition is complete, 200 ml of acetone are introduced in the drip funnel and added in the reaction flask. The stirring is maintained for 15 minutes at 120–130 rpm, then the stirring fastness is reduced to 60/80 RPM maintaining the temperature at 20±2° C. for 60 minutes. The reaction mixture is then filtered and the recovered solid product is washed with 1800 ml of acetone (450 ml for 4 times). The so obtained product is dried for 6 hours at 60–75° C.

85 g of the sodium salt of 6-[D(−)-α-(4-ethyl-2,3-dioxo-1-piperazinecarbonylamino) phenylacetamido]penicillanic acid are obtained (yield=85% by wt.; sodium salt content by HPLC (anhydrous basis) 98.50%).

What is claimed is:

1. A process for the preparation of the sodium salt of 6[D-(−)-4-(ethyl-2,3-dioxo-1-piperazinecarbonylamino) phenylacetamido]penicillanic acid, comprising the reaction of a solution of 6[D-(−)-4-(ethyl-2,3-dioxo-1-piperazinecarbonylamino) phenylacetamido]penicillanic acid in an organic solvent with a solution of a reagent selected from the group consisting of sodium hydroxide, sodium carboxylates and sodium alcoholates in an organic solvent, followed by the separation by precipitation of the resulting sodium salt, wherein said solutions are prepared in a non-sterile environment and subjected to sterilizing filtration, and the penicillanic acid sodium salt is precipitated in a sterile environment by addition of a suitably sterilized non-solvent.

2. The process according to claim 1, wherein said solution of penicillanic acid is pre-salified with an organic base.

3. The process according to claim 1, wherein said reagent is sodium 2-ethyl hexanoate.

4. The process according to claim 1, wherein said reagent is a sodium alcoholate selected from the group consisting of sodium methoxide and sodium ethoxide.

5. The process according to claim 1, wherein, when said reagent is a sodium alcoholate, the salt precipitation reaction is carried out at −10° to −30° C.

6. The process according to claim 1, wherein, when said reagent is a sodium carboxylate, the salt precipitation reaction is carried out at 15° to 25° C.

7. The process according to claim 2, wherein said organic base is selected from the group consisting of diethylamine and triethylamine.

8. The process according to claim 1, wherein the concentration of the solution of said penicillanic acid ranges from 2% to 10% by wt. in respect of the total volume of this acid solution.

9. The process according to claim 8, wherein said concentration ranges from 5% to 6% by wt.

10. The process according to claim 1, wherein the concentration of the solution of said reagent is comprised between 2% and 10% by wt. in respect of the total volume of the basic solution.

11. The process according to claim 2, wherein the concentration of the solution of the acid pre-salified with an organic base is up to 50% by wt. in respect of the total volume of this solution.

12. The process according to claim 11, wherein the said concentration of the solution of the acid pre-salified is comprised between 30 and 50% by wt. in respect of the total volume of this solution.

13. The process according to claim 1, wherein the concentration of said sodium salt solution of the acid is up to 20% by wt. in respect of the total volume of this solution.

14. The process according to claim 13, wherein said concentration of the sodium salt solution of the acid is comprised between 10 and 20% by wt. in respect of the total volume of this solution.

15. The process according to claim 1, wherein the amount of said reagent ranges from 1.0 to 1.1 mol per mol of said penicillanic acid.

16. The process according to claim 15, wherein the amount of said reagent is 1.02 mol per mol of said penicillanic acid.

17. The process according to claim 1, wherein the solution of said penicillanic acid is a solution in an organic solvent selected from the group consisting of acetone, acetonitrile, alcohols and mixtures thereof.

18. The process according to claim 17, wherein said organic solvent is acetone.

19. The process according to claim 1, wherein the solution of said reagent is a solution of 2-ethylhexanoate in an organic solvent selected from the group consisting of ethyl acetate, acetone, acetonitrile, isopropyl alcohol and mixtures thereof.

20. The process according to claim 19, wherein said organic solvent is ethyl acetate.

21. The process according to claim 1, wherein the solution of said reagent is a solution of a reagent selected from the group consisting of sodium hydroxide, sodium methoxide and sodium ethoxide in an organic solvent selected from the group consisting of alcohols.

22. The process according to claim 21, wherein said organic solvent is selected from ethanol and methanol.

23. The process according to claim 22, wherein said organic solvent is ethanol.

24. The process according to claim 1, wherein said non-solvent is selected from the group consisting of acetone, methyl isobutyl ketone, acetonitrile, ethyl acetate and mixtures thereof.

* * * * *